United States Patent
Akahane et al.

(10) Patent No.: US 11,185,309 B2
(45) Date of Patent: Nov. 30, 2021

(54) CONTROL DEVICE OF ULTRASOUND DIAGNOSTIC APPARATUS AND CONTROL METHOD FOR ULTRASOUND DIAGNOSTIC APPARATUS

(71) Applicant: KONICA MINOLTA, INC., Tokyo (JP)

(72) Inventors: Mutsuhiro Akahane, Tokyo (JP); Yasuhiro Nakamura, Kanagawa (JP); Yosuke Kimura, Tokyo (JP); Kazuya Osada, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 764 days.

(21) Appl. No.: 15/790,474

(22) Filed: Oct. 23, 2017

(65) Prior Publication Data

US 2018/0125456 A1 May 10, 2018

(30) Foreign Application Priority Data

Nov. 8, 2016 (JP) .............................. JP2016-218211

(51) Int. Cl.
*A61B 8/00* (2006.01)
*G01S 15/89* (2006.01)
(Continued)

(52) U.S. Cl.
CPC ............ *A61B 8/488* (2013.01); *A61B 8/5207* (2013.01); *A61B 8/5269* (2013.01); *A61B 8/54* (2013.01);
(Continued)

(58) Field of Classification Search
CPC ......... A61B 8/488; A61B 8/56; A61B 8/5207; A61B 8/5269; A61B 8/54; A61B 8/06;
(Continued)

(56) References Cited

U.S. PATENT DOCUMENTS 9,162,255 B1 * 10/2015 Stice .................... A61B 8/5207
9,814,447 B2    11/2017 Nakaya et al.
(Continued)

FOREIGN PATENT DOCUMENTS

JP       05130992 A    5/1993
JP    2007029198 A    2/2007
(Continued)

OTHER PUBLICATIONS

Japanese Office Action (and English language translation thereof) dated Jun. 9, 2020 issued in Japanese Application No. 2016-218211.

*Primary Examiner* — Joanne M Hoffman
*Assistant Examiner* — Milton Truong
(74) *Attorney, Agent, or Firm* — Holtz, Holtz & Volek PC

(57) ABSTRACT

Control device 10 of an ultrasound diagnostic apparatus includes a hardware processor that sets, among a plurality of operation modes in which pulse waveforms of ultrasound pulses to be transmitted are different from one another, at least first and second operation modes for which observation results are to be simultaneously displayed on a screen, sets at least one operation type that defines transmission timing of ultrasound pulses, and sets a switching frequency of a switching signal.

6 Claims, 13 Drawing Sheets

(51) Int. Cl.
*A61B 8/08* (2006.01)
*G01S 7/28* (2006.01)

(52) U.S. Cl.
CPC .................. *A61B 8/56* (2013.01); *G01S 7/28* (2013.01); *G01S 15/8979* (2013.01)

(58) Field of Classification Search
CPC ..................... G01S 7/28; G01S 15/105; G01S 15/8979–8988
See application file for complete search history.

(56) References Cited

U.S. PATENT DOCUMENTS

| | | | | |
|---|---|---|---|---|
| 2006/0094960 | A1* | 5/2006 | Phung | A61B 8/56 600/437 |
| 2007/0239001 | A1* | 10/2007 | Mehi | G01S 15/8927 600/437 |
| 2010/0022885 | A1* | 1/2010 | Wu | A61B 8/4427 600/453 |
| 2011/0040188 | A1* | 2/2011 | Tamura | A61B 8/08 600/454 |
| 2011/0176388 | A1* | 7/2011 | Brock-Fisher | H02M 1/44 367/87 |
| 2013/0345564 | A1* | 12/2013 | Nakaya | A61B 8/5246 600/441 |
| 2016/0199040 | A1* | 7/2016 | Kim | B06B 1/067 600/437 |

FOREIGN PATENT DOCUMENTS

| | | | |
|---|---|---|---|
| JP | 4657044 B2 * | 3/2011 | ............... A61B 8/06 |
| JP | 2014000290 A | 1/2014 | |
| JP | 2014068980 A | 4/2014 | |
| WO | 2013137061 A1 | 9/2013 | |
| WO | WO-2013137061 A1 * | 9/2013 | ........... A61B 8/5215 |
| WO | WO-2015076439 A1 * | 5/2015 | ......... G01S 15/8979 |

\* cited by examiner

CONTROL DEVICE OF ULTRASOUND DIAGNOSTIC APPARATUS AND CONTROL METHOD FOR ULTRASOUND DIAGNOSTIC APPARATUS

CROSS REFERENCE TO RELATED APPLICATIONS

This application is entitled to and claims the benefit of Japanese Patent Application No. 2016-218211, filed on Nov. 8, 2016 and the disclosure, of which including the specification, drawings and abstract is incorporated herein by reference in its entirety.

BACKGROUND

Technological Field

The present invention relates to a control device and a control method for ultrasound diagnostic apparatus.

Description of Related Art

A DC/DC converter of a switching drive system that is small and has high conversion efficiency is generally used as a power generation device of an ultrasound diagnostic apparatus. It has been, however, known that because such a DC/DC converter of a switching drive system produces an operating voltage by switching on and off of a switching element at a frequency of from several hundred kHz to several MHz, an electromagnetic noise and/or a conductive noise occur at the switching frequency and at frequencies of high-order harmonics of the switching frequency (hereinafter, also referred to as "switching noise").

It has been known, in ultrasound diagnostic apparatuses, that the switching noise is superimposed on a frequency band in which a Doppler shift frequency is observed, particularly during detection of a blood flow velocity pattern and the like by a pulsed Doppler method (hereinafter, referred to as "PW Doppler" method). As a result, there is a risk that the switching noise appears in a screen where the blood flow velocity pattern and the like are displayed, thereby hindering accurate diagnosis.

Japanese Patent Application Laid-Open No. H5-130992, for example, proposes a method for controlling a switching frequency of a switching power supply such that the switching frequency is an integer multiple of a pulse repetition frequency to prevent such a switching noise from appearing on a screen.

In addition, Japanese Patent Application Laid-Open No. 2007-029198 proposes a method for controlling a switching frequency such that neither a fundamental frequency of a switching signal nor harmonics of the fundamental frequency is included in a frequency band in which a Doppler shift frequency is observed.

However, depending on a flow velocity range (range within which a Doppler shift frequency is observed) applied in detection of a blood flow velocity pattern and the like, there are dozens of patterns of pulse repetition frequencies each of which is a frequency at which ultrasound pulses are transmitted. It is therefore difficult to set a switching frequency of a switching power supply for every pulse repetition frequency such that the switching frequency is an integer multiple of the pulse repetition frequency, in spite of the proposal of the conventional technique of Japanese Patent Application Laid-Open No. H5-130992.

In addition, in a case, for example, where a flow velocity range to be applied in detection of a blood flow velocity pattern and the like is desired to be expanded, it may be difficult to set a switching frequency such that no switching frequency is within any of the frequency bands where a switching noise is to be included, in spite of the proposal of the conventional technique of Japanese Patent Application Laid-Open No. 2007-029198.

In particular, it has been made possible in recent years to carry out a plurality of operation modes in combination by switching transmission timing of ultrasound pulses (hereinafter, referred to as "combined operation mode"), and setting a more preferable switching frequency in consideration of aspects of carrying out such a combined operation mode has been desired.

SUMMARY

An object of the present disclosure is to provide a control device and a control method for an ultrasound diagnostic apparatus which makes it possible to reduce mixing of a switching noise in a detection result of a Doppler shift frequency particularly in a combined operation mode.

A control device of an ultrasound diagnostic apparatus in which one aspect of the present invention is reflected in an attempt to at least partly achieve the above-mentioned object is a control device of an ultrasound diagnostic apparatus, the ultrasound diagnostic apparatus having a switching power supply that produces an operational voltage, the ultrasound diagnostic apparatus being configured to transmit an ultrasound pulse repeatedly and to be capable of detecting a Doppler shift frequency from an ultrasound echo reflected from an inside of a subject, the control device including a hardware processor that: sets, from among a plurality of operation modes in which pulse waveforms of ultrasound pulses to be transmitted are different from one operation mode to another, at least first and second operation modes for which observation results are to be simultaneously displayed on a screen; sets at least one operation type that defines transmission timing of ultrasound pulses in each of the first and the second operation modes; and sets a switching frequency of a switching signal used for driving the switching power supply, such that neither a fundamental frequency nor a harmonic of the switching signal is included in a Doppler observation frequency band to be determined based on the first and the second operation modes and on the operation types.

A control method for an ultrasound diagnostic apparatus in which one aspect of the present invention is reflected in an attempt to at least partly achieve the above-mentioned object is a control method for an ultrasound diagnostic apparatus, the ultrasound diagnostic apparatus having a switching power supply that produces an operational voltage, the ultrasound diagnostic apparatus being configured to transmit an ultrasound pulse repeatedly and to be capable of detecting a Doppler shift frequency from an ultrasound echo reflected from an inside of a subject, the control method including: setting, from among a plurality of operation modes in which pulse waveforms of ultrasound pulses to be transmitted are different from one operation mode to another, at least first and second operation modes for which observation results are to be simultaneously displayed on a screen; setting at least one operation type that defines transmission timing of ultrasound pulses in each of the first and the second operation modes; and setting a switching frequency such that neither a fundamental frequency nor a harmonic of the switching signal used for driving the switching power supply is included in a Doppler observation frequency band to be determined based on the first and the second operation modes and on the operation types.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

(Configuration of Ultrasound Diagnostic Apparatus)

Hereinafter, a configuration of ultrasound diagnostic apparatus A according to one embodiment of the present invention is described with reference to FIGS. 1, 2, 3A, and 3B.

Figure 1:
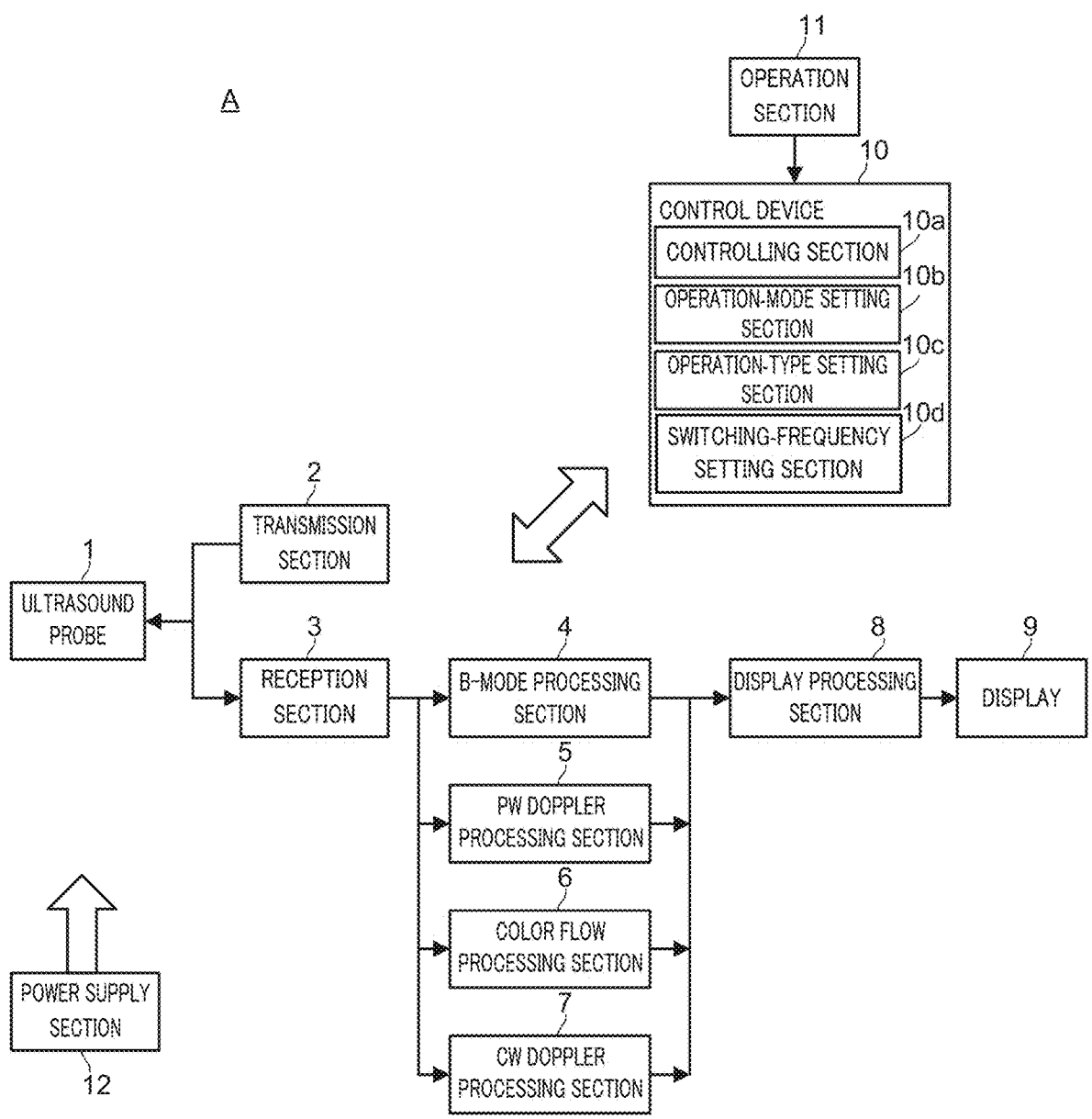
FIG. 1 illustrates an example of signal-processing courses in an entire configuration of an ultrasound diagnostic apparatus according to an embodiment of the invention.
Figure 2:
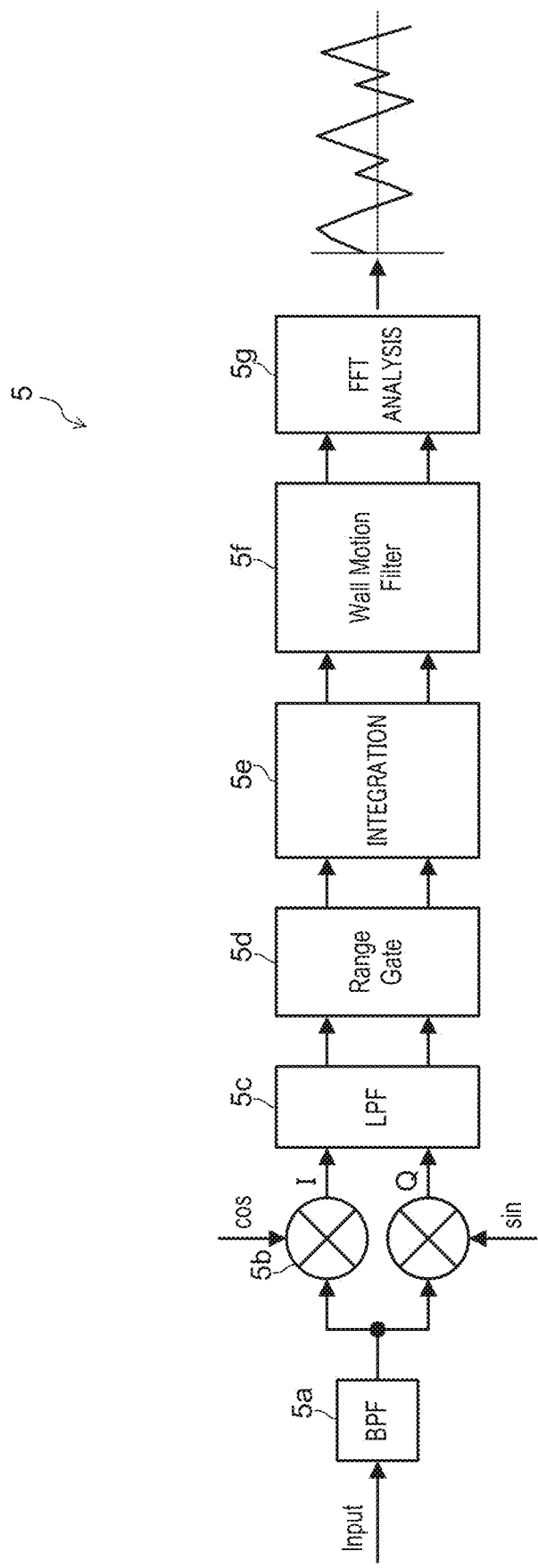
FIG. 2 illustrates an example of a configuration of a PW Doppler processing section of the ultrasound diagnostic apparatus according to the embodiment of the invention.
Figure 3A:
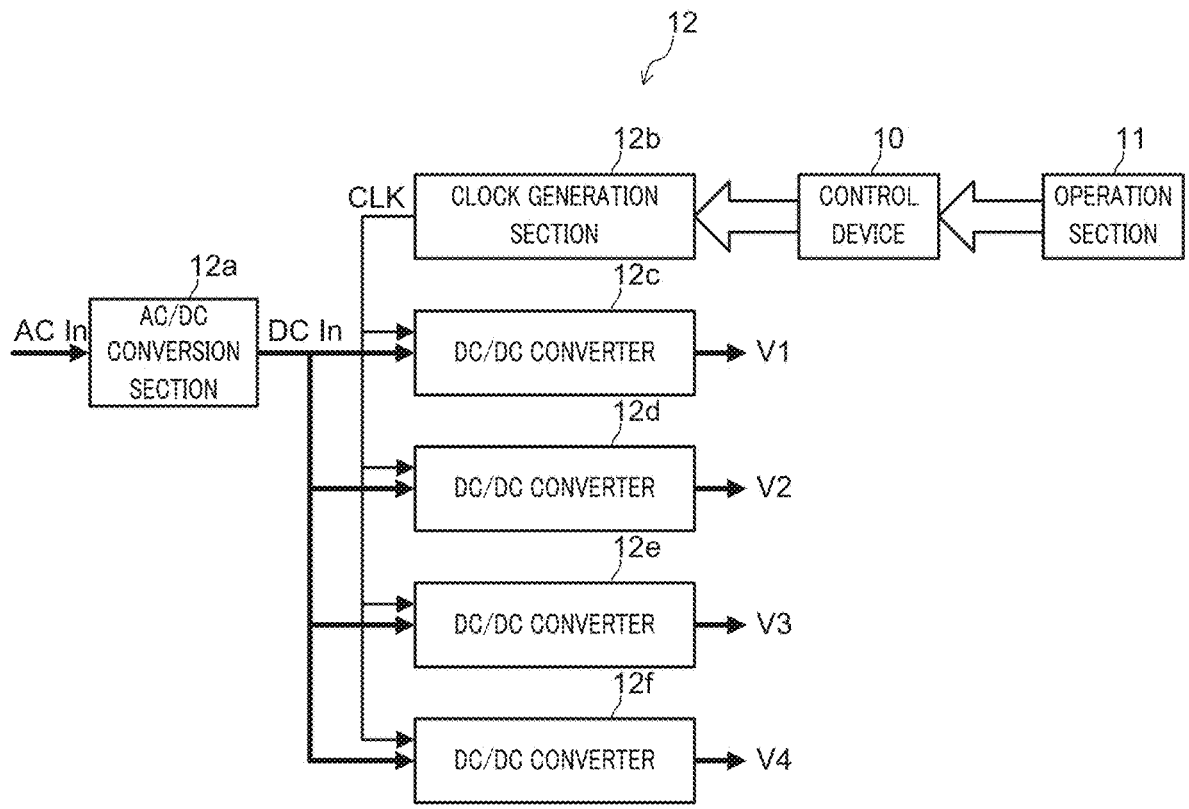
FIGS. 3A and 3B illustrate an example of a configuration of a power supply section of the ultrasound diagnostic apparatus.
Figure 3B:
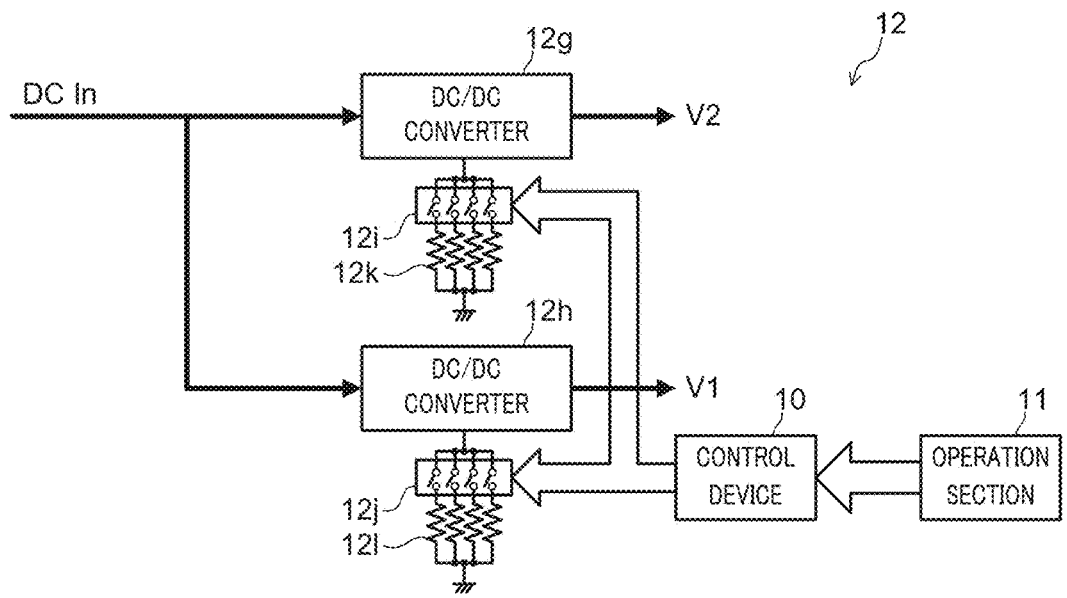

FIG. 1 illustrates an example of signal-processing courses in an entire configuration of ultrasound diagnostic apparatus A according to the present embodiment of the invention. FIG. 2 illustrates an example of a configuration of PW Doppler processing section 5 of ultrasound diagnostic apparatus A according to the present embodiment of the invention. FIGS. 3A and 3B illustrate an example of a configuration of power supply section 12 of ultrasound diagnostic apparatus A.

Ultrasound diagnostic apparatus A according to the present embodiment is configured to include ultrasound probe 1, transmission section 2, reception section 3, B-mode processing section 4, PW (Pulse Wave) Doppler processing section 5, color flow processing section 6, CW (Continuous Wave) Doppler processing section 7, display processing section 8, display 9, control device 10, operation section 11, and power supply section 12. Note that power supply section 12 in the present embodiment corresponds to the above-mentioned "switching power supply."

Ultrasound probe 1 converts an electric pulse generated in transmission section 2 into an ultrasound pulse, transmits the ultrasound pulse into a subject, receives an ultrasound echo reflected on the inside of a subject, converts the ultrasound echo into an electric signal, and outputs the electric signal to reception section 3. Ultrasound probe 1 is configured to include a plurality of transducers (piezoelectric elements) which are, for example, one- or two-dimensionally disposed, and a channel switching section (selector) for switching control between on and off of the driving states of the plurality of transducers individually or on a block basis (hereinafter, referred to as "channel").

In the meantime, ultrasound probe 1 transmits ultrasound pulses into the subject in the order along the scanning direction by sequentially driven channels to be driven among the plurality of channels (by scanning) when two-dimensional data are generated in the B mode or in the color flow mode.

Transmission section 2 is a transmitter configured to send out a voltage pulse that is a driving signal to ultrasound probe 1. Transmission section 2 is configured to include a high-frequency pulse oscillator, a pulse setting section, and the like, for example. Transmission section 2 adjusts the voltage pulses generated in the high-frequency pulse oscillator to a voltage amplitude, pulse width, and timing set by the pulse setting section, and then send out the voltage pulses for each of the channels of ultrasound probe 1.

Transmission section 2 includes the pulse setting section for each of the plurality of channels of ultrasound probe 1, and the voltage amplitude, pulse width, and timing of voltage pulses can be set separately for each of the plurality of channels. For example, transmission section 2 sets delay times suitable for the plurality of channels to change a target depth and/or to generate different pulse waveforms (for example, one-wave pulse is sent out in the B mode and four-wave pulse is sent out in the PW Doppler mode).

Reception section 3 is an ultrasound receiver configured to perform reception processing of an electric signal related to an ultrasound echo and generated by ultrasound probe 1. Reception section 3 is configured to include a preamplifier for each channel, an A/D conversion section for each channel, a reception beamformer, and a processing system switching section.

The preamplifier of reception section 3 amplifies the electric signal related to a weak ultrasound echo. The A/D conversion section converts the amplified electric signal into a digital signal. The reception beamformer unifies signals of the plurality of channels by phasing and adding of received signals of the channels, to thereby generate a signal to be processed by a processing section in the later part of processing (referred to as "reception signal").

The processing system switching section of reception section 3 switches sections to which the reception signal is outputted, and outputs the reception signal generated by the reception beamformer to one of B-mode processing section 4, PW Doppler processing section 5, color flow processing section 6, and CW Doppler processing section 7 depending on an operation mode to be carried out.

Figure 4B:
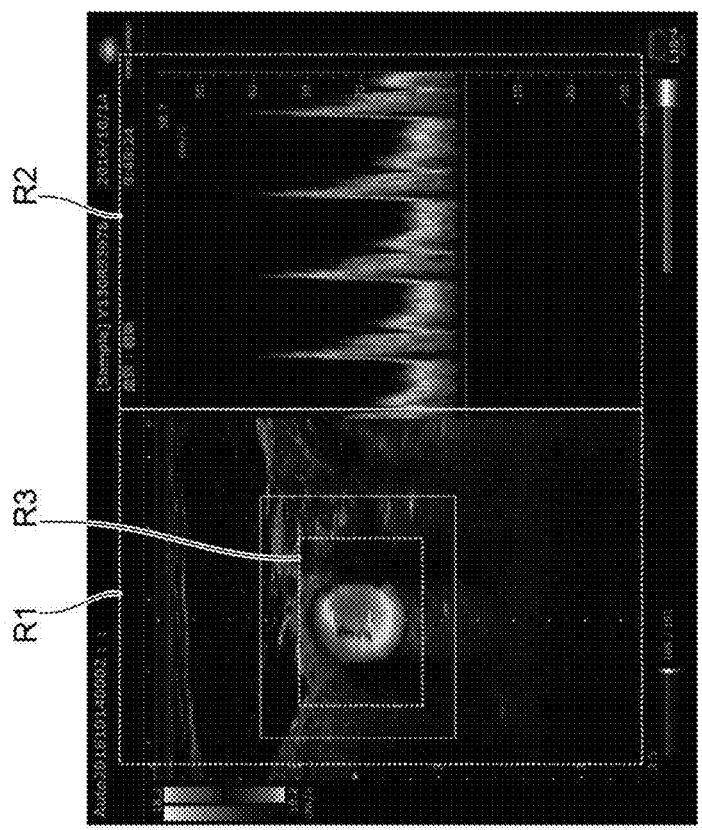
FIGS. 4A and 4B each illustrate an example of an image generated in a combined operation mode.
Figure 4A:
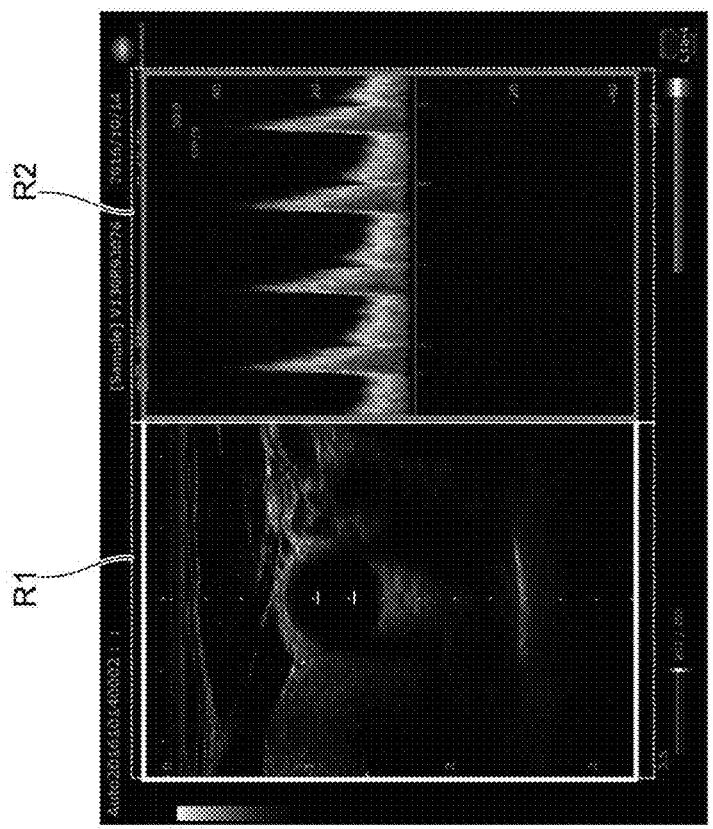

B-mode processing section 4 obtains a reception signal from reception section 3 during a B-mode operation, and generates a B-mode image that is a tomographic image of the inside of a subject (see FIGS. 4A and 4B).

For example, B-mode processing section 4 accumulates, in a line memory, the temporal variation of intensities of an ultrasound echo detected after ultrasound probe 1 transmits an ultrasound pulse in the depth direction. Along with scanning by using ultrasound pulses from ultrasound probe, B-mode processing section 4 successively accumulates the temporal variation of the intensities of the ultrasound echo at each scanning position in the line memory, to thereby generate two-dimensional data used as a frame unit. Then, B-mode processing section 4 generates the B-mode image by converting, into a brightness value, the intensities of the ultrasound echo detected at each position of the inside of the subject.

B-mode processing section 4 is configured to include an envelope detection circuit, a dynamic filter, and a logarithmic compression circuit, for example. The envelope detection circuit carries out envelope detection of the reception signal to detect the intensity. The logarithmic compression circuit performs logarithmic compression to the intensity of the reception signal detected in the envelope detection circuit. The dynamic filter is a bandpass filter in which the frequency characteristics are changed depending on depths, detects an echo signal depending on the attenuation of ultrasonic frequency by the living body, and removes a noise component by cutting off a reception signal including no echo signal.

PW Doppler processing section 5 obtains a reception signal from reception section 3 during a PW Doppler mode operation to generate a frequency spectrum image (hereinafter, also referred to as "blood flow velocity pattern") of a Doppler shift frequency of an ultrasound echo from flowing blood and/or a moving body tissue (see FIGS. 2, 4A, and 4B).

In the case where ultrasound pulses are transmitted repeatedly, for example, PW Doppler processing section 5 samples reception signals related to ultrasound echoes, in synchronization with the pulse repetition frequency of the ultrasound pulses. In other words, in the case where ultrasound pulses are transmitted and received at constant intervals in accordance with the pulse repetition frequency, PW Doppler processing section 5 estimates a Doppler shift frequency based on a phase difference between an $n^{th}$ ultrasound echo and $n+1^{th}$ ultrasound echo from the same sample gate depth (position of observation object in the depth direction; the same applies hereinafter).

PW Doppler processing section 5 is configured to include bandpass filter 5a, quadrature detection section 5b, low pass filter 5c, range gate 5d, integration circuit 5e, wall motion filter 5f, and FFT analysis section 5g, for example. Bandpass filter 5a removes an unnecessary frequency component. Quadrature detection section 5b generates a quadrature-detection signal by mixing, with a reception signal, a reference signal being in phase with a transmitted ultrasound pulse and a reference signal being π/2 out of phase with the transmitted ultrasound pulse. Low pass filter 5c removes a high frequency component of the quadrature-detection signal to generate a reception signal related to a Doppler shift frequency. Range gate 5d obtains only an ultrasound echo from a sample gate depth. Integration circuit 5e integrates the reception signals obtained by range gate 5d. Wall motion filter 5f carries out processing of removal of a clutter component (ultrasound echo from a tissue) by removal of components at a low frequency region. FFT analysis section 5g performs a frequency analysis of the Doppler shift frequency component of the reception signal obtained as described above.

Color flow processing section 6 obtains a reception signal from reception section 3 during a color flow mode operation, and generates a color flow image representing the velocity, power, and velocity turbulence of flowing blood and/or a moving body tissue (see FIG. 4B). As in PW Doppler processing section 5, Color flow processing section 6 detects ultrasound echoes, reflected from positions at the same depth, of successively transmitted ultrasound pulses, for example. Then, color flow processing section 6 detects a Doppler shift frequency component by an analysis based on autocorrelation processing. Color flow processing section 6 generates the color flow image by expressing, by a color space vector, the velocity, power, and velocity turbulence which are converted from the Doppler shift frequencies of ultrasound echoes reflected from flowing blood and the like.

Color flow processing section 6 is configured to include a MTI filter, a quadrature-detection circuit, and an autocorrelation arithmetic section, for example (not illustrated). The MTI (Moving Target Indication) filter performs processing of removing, from the reception signal, a clutter component (ultrasound echo from a tissue) from an unmoving tissue. The quadrature detection generates a quadrature-detection signal by mixing, with the reception signal, a reference signal being in phase with a transmitted ultrasound and a reference signal being π/2 out of phase with the transmitted ultrasound. An autocorrelation arithmetic section computes the velocity, power, turbulence, and the like of flowing blood by performing autocorrelation arithmetic to the quadrature-detection signals of ultrasound echoes, reflected from positions at the same depth, of the successively transmitted ultrasound pulses.

CW Doppler processing section 7 operates during a CW Doppler mode operation, obtains a reception signal from reception section 3, and generates a frequency spectrum image of a Doppler shift frequency as in PW Doppler processing section 5. In the CW Doppler mode, unlike the PW Doppler mode, a continuous wave of constant frequency is transmitted and a Doppler shift frequency component is computed from an ultrasound echo related to the continuous wave. CW Doppler processing section 7 is configured to include a bandpass filter, a quadrature detection section, a low pass filter, and a FFT analysis section, for example.

Display processing section 8 receives image data related to the B-mode image, the frequency spectrum image, the color flow image, and the like from B-mode processing section 4, PW Doppler processing section 5, color flow processing section 6, and CW Doppler processing section 7, and outputs, to display 9, the received image data after subjected to predetermined image processing, such as coordinate conversion processing and/or data interpolation processing.

Display 9 is a monitor which displays the image data outputted from display processing section 8.

In the meantime, B-mode processing section 4, PW Doppler processing section 5, color flow processing section 6, CW Doppler processing section 7, and display processing section 8 are implemented by a digital arithmetic circuit composed, for example, of a digital signal processor (DSP). The configurations of these sections can, however, include variations, and may partially or entirely be implemented by a hardware circuit or arithmetic processing which follows a program.

Control device 10 transmits and receives control signals to and from ultrasound probe 1, transmission section 2, reception section 3, B-mode processing section 4, PW Doppler processing section 5, color flow processing section 6, CW Doppler processing section 7, display processing section 8, display 9, operation section 11, power supply section 12 and the like, so as to integrally control them. Control device 10 is configured to include, for example, a central processing unit (CPU), hard disk drive (HDD), and/or solid state drive (SSD), random access memory (RAM), and the like.

Control device 10 includes controlling section 10a, operation-mode setting section 10b, operation-type setting section 10c, and switching-frequency setting section 10d.

Controlling section 10a causes ultrasound probe 1, transmission section 2, reception section 3, B-mode processing section 4, PW Doppler processing section 5, color flow processing section 6, CW Doppler processing section 7, and the like to operate. Controlling section 10a according to the present embodiment causes ultrasound probe 1, transmission section 2, reception section 3, B-mode processing section 4, PW Doppler processing section 5, color flow processing section 6, CW Doppler processing section 7, and the like to operate, in accordance with an operation mode (for example, B mode or PW Doppler mode) set by operation-mode setting section 10b and in accordance with an operation type (for example, independent type or cooperation type) set by operation-type setting section 10c.

Operation-mode setting section 10b sets an operation mode to be carried out, from among the B-mode, color flow mode, PW Doppler mode, and CW Doppler mode, and allows controlling section 10a to carry out control according to the mode. Operation-mode setting section 10b according to the present embodiment sets, from among the plurality of operation modes, a plurality of operation modes for which observation results are to be displayed together on a screen of display 9 (described later with reference to FIGS. 4A and 4B).

Operation-type setting section 10c sets an operation type defining transmission timing of each operation mode in a case where a plurality of operation modes are carried out (described later with reference to FIGS. 5A to 5C, 6A, and 6B).

Switching-frequency setting section 10d sets a switching frequency of a switching signal which drives power supply section 12 (DC/DC converter). Switching-frequency setting section 10d according to the present embodiment sets the switching frequency so that frequencies being positive-integer multiples of the switching frequency are not included in a frequency band which is determined depending on the above-mentioned operation type and within which a Doppler shift frequency is observed (hereinafter, referred to as a "Doppler observation frequency band") (described later with reference to FIGS. 10 to 12).

Figure 13:
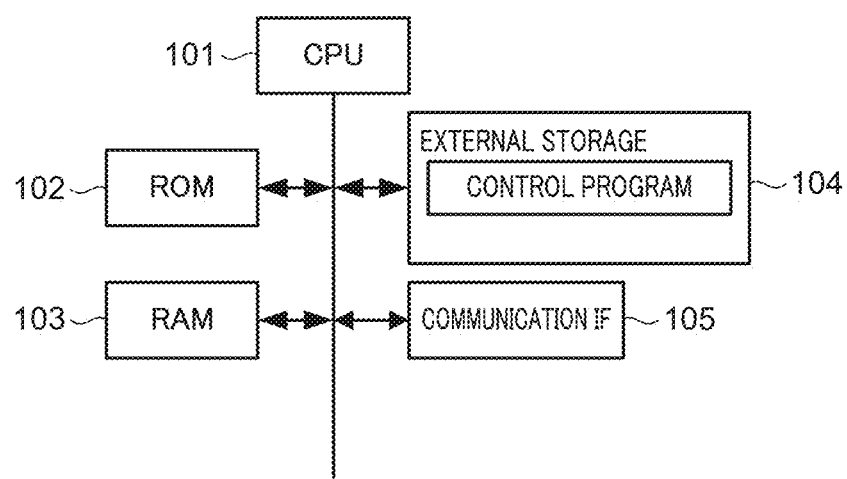
FIG. 13 illustrates an example of a hardware configuration of the control device of the ultrasound diagnostic apparatus according to the embodiment of the invention.

FIG. 13 illustrates an example of a hardware configuration of control device 10 according to the present embodiment.

Control device 10 is a computer including, as main components, CPU 101, ROM 102, RAM 103, external storage (for example, flash memory) 104, communication interface 105, and the like.

Note that the above-mentioned functions are implemented, for example, by the CPU referring to control programs and/or various data recorded on HDD, SSD, RAM, and/or the like. Implementation of the functions, however, is not limited to processing by software, and the functions may partially or entirely be implemented by a dedicated hardware circuit.

Operation section 11 is a user interface for an input operation by an operator, and is composed, for example, of a push-button switch, keyboard, mouse, touch panel, and the like. Operation section 11 converts the input operation made by the operator into an operation signal, and inputs the operation signal into control device 10. A sample gate depth for detection of a blood flow velocity pattern in the PW Doppler mode can be set by operation section 11, for example.

Power supply section 12 generates a power supply voltage of direct current for operation of each of the above-mentioned sections, and supplies electricity to the sections. In power supply section 12 according to the present embodiment, a DC/DC converter of a switching drive system in which a switching frequency is variable is used. In this respect, power supply section 12 only has to be a DC/DC converter of the switching drive system, and may be a DC/DC converter of any circuit system (for example, a half bridge type, a chopper type, or the like). A drive system of a switching element may also be either of a pulse width modulation (PWM) drive system or a pulse frequency modulation (PFM) drive system. Note that detailed descriptions for the DC/DC converter are omitted here since the configuration of the DC/DC converter is well known.

In this respect, a duty ratio of when a switching element is switched on and off is controlled by feedback control, so that the voltage outputted from the DC/DC converter is adjusted to a predetermined value (in the case of the PWM drive system), for example. In this case, a switching frequency is set as a frequency of a switching signal to be used for duty ratio control, for example.

Power supply section 12 according to the present embodiment is configured such that the switching frequency is variable depending on a control signal from control device 10 by the configuration illustrated in FIGS. 3A and 3B.

FIG. 3A illustrates the DC/DC converter configured to be synchronized with an external clock.

In FIG. 3A, DC/DC converters 12c to 12f are each configured to switch on and off of the switching element based on a clock signal from clock generation section 12b, so as to convert a direct current voltage supplied from AC/DC conversion section 12a to output the converted voltage. In this case, the switching frequency is made variable depending on a value set in a frequency setting register of clock generation section 12b by control device 10, for example. DC/DC converters 12c to 12f are here provided to generate output voltages different from one another.

FIG. 3B illustrates DC/DC converters each configured to include a built-in oscillator.

In FIG. 3B, DC/DC converters 12g and 12h are each configured to switch on and off of a switching element based on a clock signal of the built-in oscillator, so as to convert a supplied direct current voltage to output the converted voltage. In this case, the opened or closed states of switch circuits 12i and 12j are switched by control device 10 and external resistances 12k and 12l connected to the built-in oscillators are thus switched, so that the switching frequency is controlled.

(Operation Mode and Operation Type of Ultrasound Diagnostic Apparatus)

Hereinafter, operation modes and operation types of ultrasound diagnostic apparatus A are described with reference to FIGS. 4A, 4B, 5A to 5C, 6A, and 6B.

Operation modes of ultrasound diagnostic apparatus A according to the present embodiment include the B mode, color flow mode, PW Doppler mode, and CW Doppler mode. Ultrasound diagnostic apparatus A (controlling section 10a) causes transmission section 2 to transmit an ultrasound pulse in a mode corresponding to an operation mode, causes reception section 3 to receive an ultrasound echo, and causes a processing section corresponding to the operation mode among B-mode processing section 4, PW Doppler processing section 5, color flow processing section 6, and CW Doppler processing section 7 to process a reception signal.

An ultrasonic pulse waveform to be transmitted is different for each operation mode to be carried out, and one of the operation modes is to be carried out. In the "combined operation mode," however, it is possible to display, on display 9 at the same time, images (observation results) generated in a plurality of operation modes by applying different transmission timing of ultrasound pulses for each of the operation modes.

FIG. 4A illustrates an example of an image generated when two of B mode and PW Doppler mode are carried out in the combined operation mode. FIG. 4B illustrates an example of an image generated when three of B mode, PW Doppler mode, and color flow mode are carried out in the combined operation mode.

In each of FIGS. 4A and 4B, a B-mode image generated in the B mode is displayed in the R1 region and a frequency spectrum image generated in the PW Doppler mode is displayed in the R2 region. FIG. 4B illustrates a state where a color flow image generated in the color flow mode is further displayed in addition to the B-mode image and the frequency spectrum image in the R3 region superimposed on the R1 region.

In FIGS. 4A and 4B, images generated in a plurality of operation modes are displayed at the same time by application of different transmission timing for each operation mode.

Note that, in each of FIGS. 4A and 4B, the vertical axis of the B-mode image (R1 region) corresponds to the depth direction, and the horizontal axis corresponds to the scanning direction. In addition, the vertical axis of the frequency spectrum image (R2 region) corresponds to the blood flow velocity (the line at a position in the middle of the vertical axis indicates a velocity of 0), and the horizontal axis corresponds to time.

The color flow image (R3 region) represents, in the RGB color space, blood flow velocities of corresponding positions in the B-mode image. In the color flow image, the brightness value of R component is expressed in such a manner as to increase with increasing velocity of blood flowing towards ultrasound probe 1, and, in contrast, the brightness value of B component is expressed in such a manner as to increase with increasing velocity of blood flowing away from ultrasound probe 1.

As mentioned above, operation-type setting section 10c of ultrasound diagnostic apparatus A sets an operation type which defines the transmission timing of ultrasound pulses for each operation mode when a plurality of operation modes are carried out in the combined operation mode.

In a case where the PW Doppler mode and the B mode are carried out in the combined operation mode, for example, operation-type setting section 10c sets, as an operation type, from an independent type in which only ultrasound pulses related to the PW Doppler mode are successively transmitted (updated), a cooperation type in which while the ultrasound pulses related to the PW Doppler mode are transmitted, an ultrasound pulse related to the B mode is transmitted between transmission of the ultrasound pulses related to the PW Doppler mode (for example, the ultrasound pulse related to the B mode and the ultrasound pulse related to the PW Doppler mode are alternately transmitted), and an MSE type in which the ultrasound pulses related to the PW Doppler mode are successively transmitted, and data of when the ultrasound pulse according to the B mode is transmitted and which is to be generated in the PW Doppler mode is interpolated, for example, by linear prediction. Note that the operation types can each be subdivided into a plurality of subtypes by the number of times of transmission of ultrasound pulses related to the B mode between the $n^{th}$ and the $n+1^{th}$ transmission of ultrasound pulses related to the PW Doppler mode.

Figure 5A:
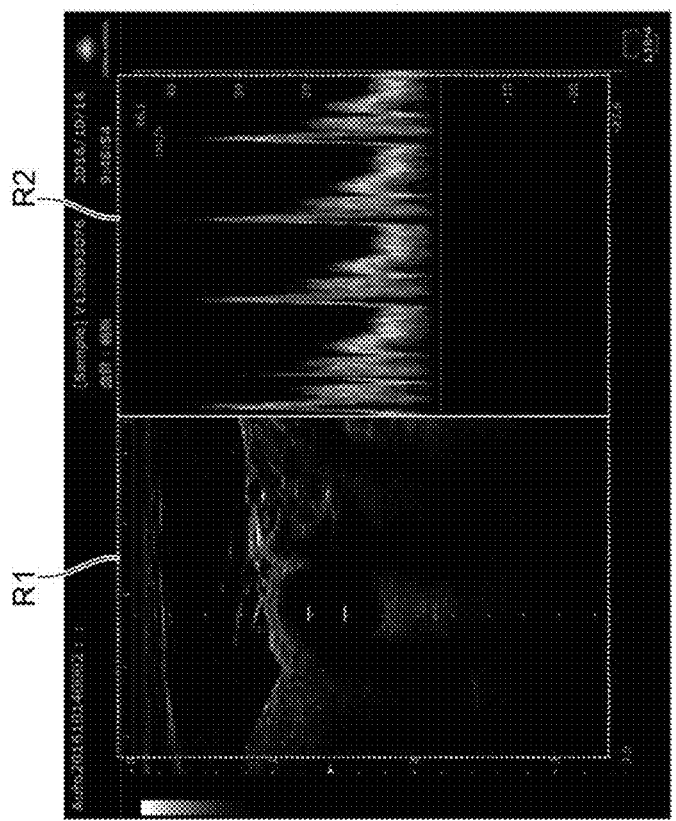
FIGS. 5A to 5C are images for explanation of operation types in the combined operation mode.
Figure 5A:
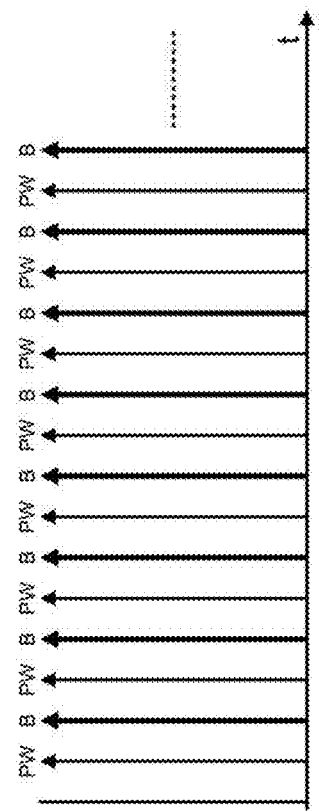
Figure 5B:
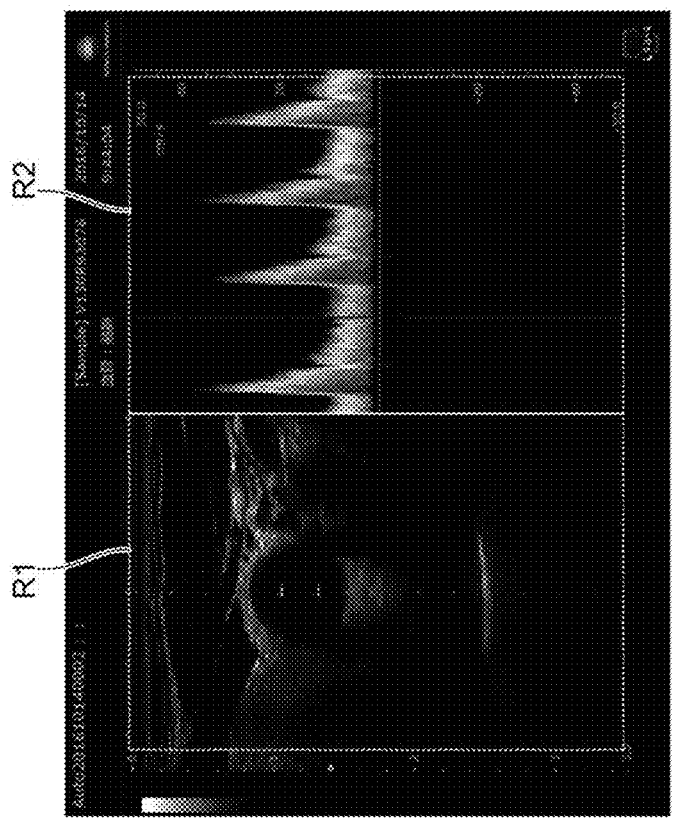
Figure 5B:
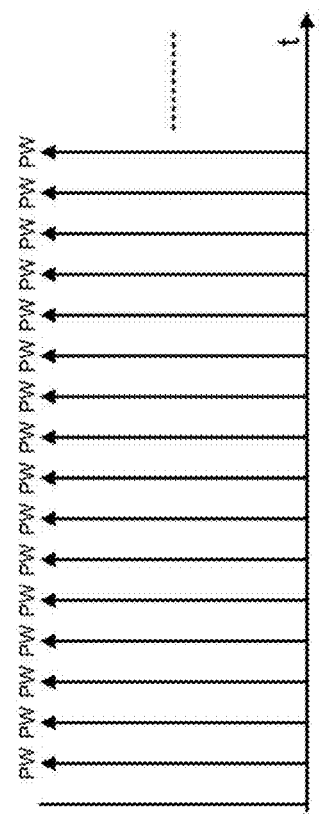
Figure 5C:
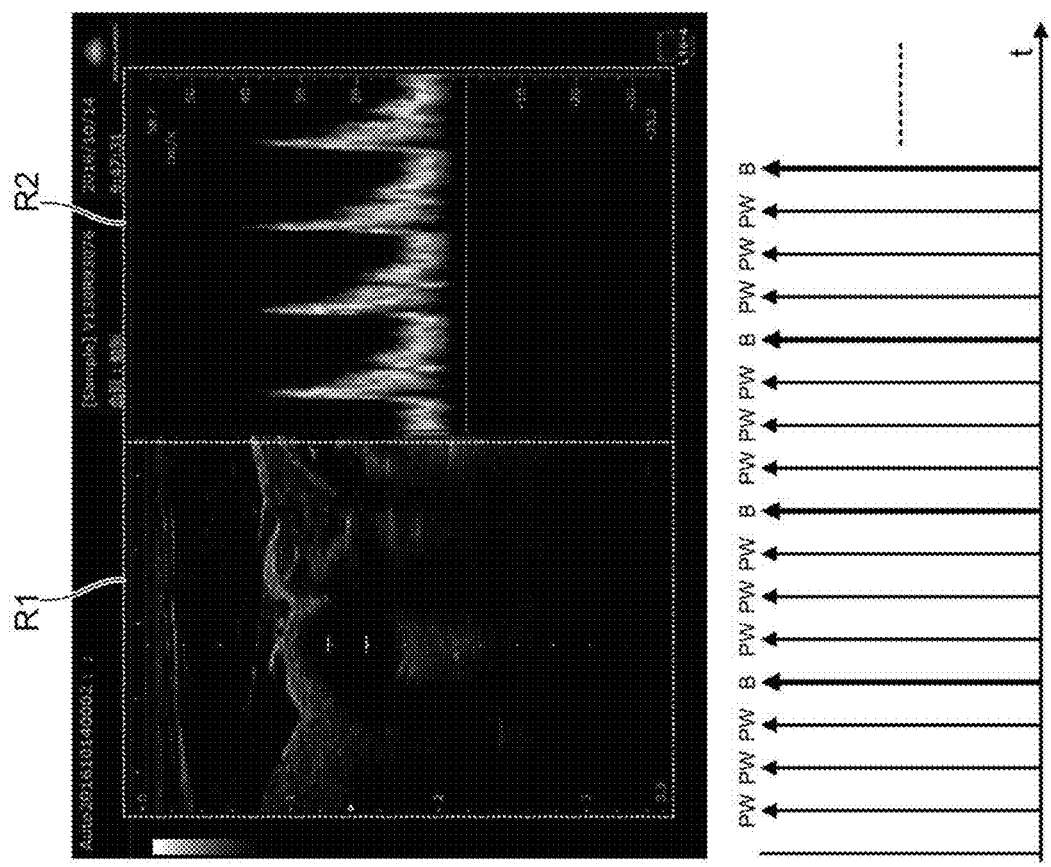

FIGS. 5A to 5C are images for explaining operation types of a case where two of the PW Doppler mode and the B mode illustrated in FIG. 4A are carried out in the combined operation mode.

FIG. 5A is an image for explaining a mode in which the PW Doppler mode of the independent type are carried out. FIG. 5B is an image for explaining a mode in which the PW Doppler mode and the B mode of the cooperation type are carried out. FIG. 5C is an image for explaining a mode in which the PW Doppler mode and the B mode of the MSE type are carried out.

The graphs in FIGS. 5A to 5C illustrate transmission timing in each mode by arrows on the time axis (horizontal axis) that are provided with letters designating each mode. Arrows PW in the figures indicate the transmission timing in the PW Doppler mode, and arrows B indicate the transmission timing in the B mode. Note that the "transmission timing" as used herein means timing of one transmission of ultrasound pulse in the corresponding mode.

In the operation type of FIG. 5A (independent type), only the PW Doppler mode are carried out successively. Accordingly, the PW Doppler mode is to be repeatedly carried out at intervals between the arrows. In other words, the intervals of the arrows represent a pulse repetition frequency in the PW Doppler mode.

In this case, the B mode is carried out, for example, before the PW Doppler mode is started. A B-mode image thus generated is retained as static image data in storage, and is displayed on display 9 as a static image.

In the case of the operation type of FIG. 5B (cooperation type), the PW Doppler mode and the B mode are carried out alternately. In this case, a B-mode image or a frequency spectrum image of the PW Doppler mode is updated every time corresponding one of these modes is carried out, and the B-mode image is also displayed on display 9 as a video image.

Note that, it is necessary to transmit and receive a plurality of ultrasound pulses to and from the same depth position (sample gate depth) in order to compute the frequency spectrum in the PW Doppler mode. Accordingly, a pulse repetition frequency of the PW Doppler mode of the cooperation type is represented by intervals between operations of the PW Doppler mode in which the B mode is carried out (intervals between arrows PW in FIG. 5B).

In the operation type of FIG. 5C (MSE type), while the PW Doppler mode is successively carried out, the B mode is carried out between some operations of the PW Doppler mode. Note, in this case however, that a reception signal at the timing of carrying out the B mode is interpolated by linear prediction or the like when a frequency analysis is made in the PW Doppler mode. Accordingly, the pulse repetition frequency of the PW Doppler mode can be set to a high value as in the example of FIG. 5A.

The above-mentioned operation types are properly used depending on the observation object and the like.

The independent type of FIG. 5A is advantageous in that a flow velocity range can be set freely in a wide range in the PW Doppler mode, and the increased number of samples for computation of a frequency spectrum in the PW Doppler mode can be obtained, thereby allowing accurate computation of the frequency spectrum. In the independent type, however, the B-mode image is not updated, so that the PW Doppler observation position (sample gate depth and transmission direction of ultrasound pulse) cannot be checked and corrected even if the observation position is displaced.

In the meantime, in the PW Doppler mode, a blood flow velocity pattern is generally corrected based on data obtained in the operation in the B mode since detection results of the blood flow velocity in the PW Doppler mode include errors depending on an angle formed between the transmission direction of an ultrasound pulse and the direction of the blood flow.

In contrast, the cooperation type of FIG. 5B is advantageous in that, in contrast to the independent type, the B-mode image is updated on a real-time basis, thereby allowing real-time checking and correction of a PW Doppler observation position (sample gate depth and transmission direction of ultrasound pulse). In the case of the cooperation type, however, the maximum pulse repetition frequency is determined depending on a period required for carrying out the B mode, thus resulting in a narrow flow velocity range in the PW Doppler. In addition, the number of samples for computation of frequency spectrum in the PW Doppler mode decreases, thus resulting in a decrease in accuracy of frequency spectrum.

In the meantime, although data of both the independent and cooperation types can be complemented in the MSE type of FIG. 5C, it is impossible to complement when a spectrum waveform largely changes, and a joint is thereby caused in the spectrum waveform at the timing of such a large change.

Figure 6B:
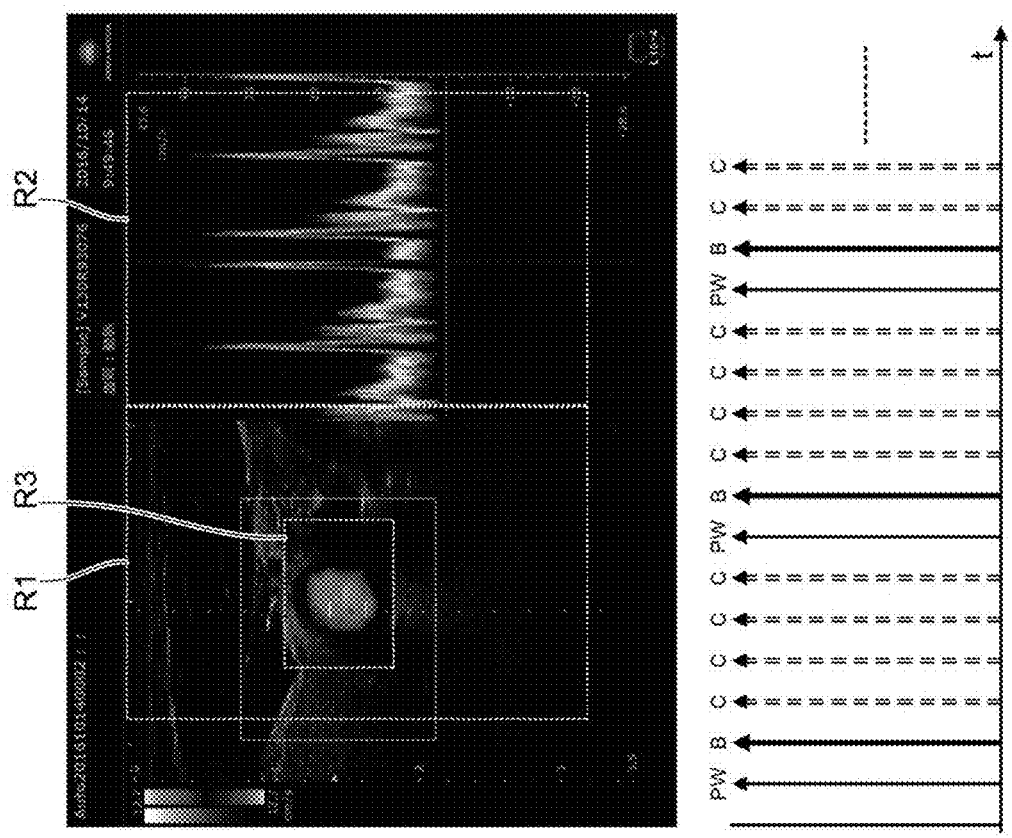
FIGS. 6A and 6B are images for explanation of the operation types in the combined operation mode.
Figure 6A:
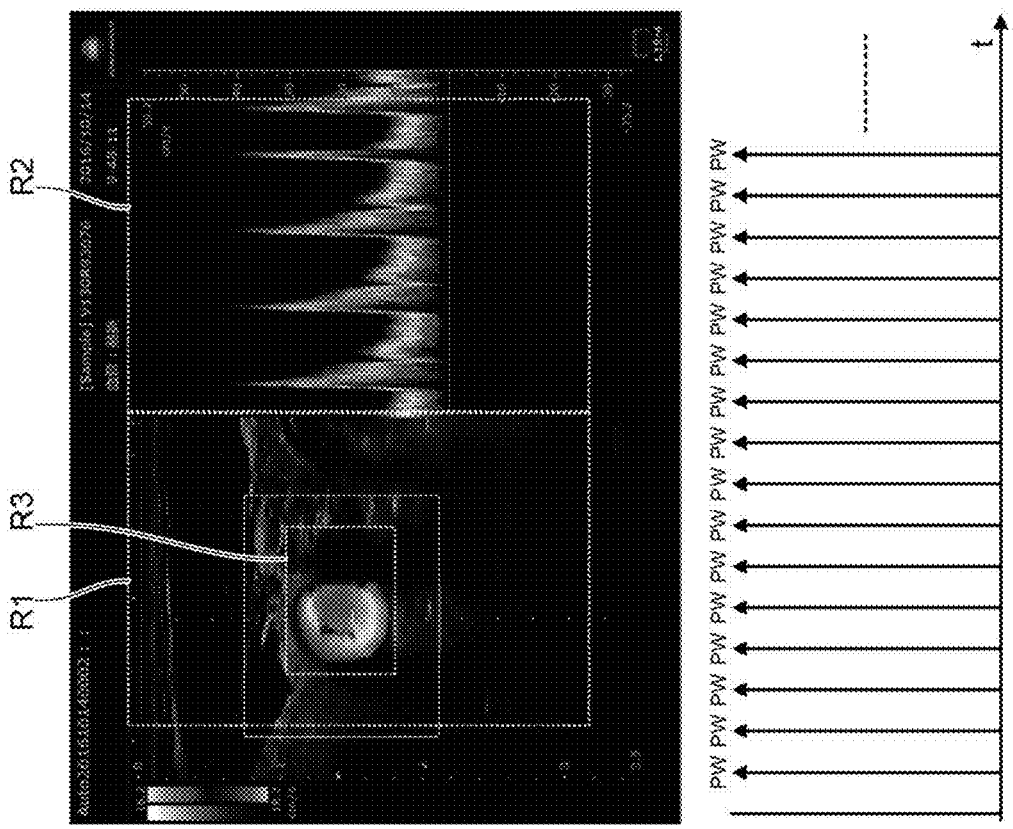

FIGS. 6A and 6B are images for explaining operation types of when three of the PW Doppler mode, the B mode, and the color flow mode illustrated in FIG. 4B are carried out in the combined operation mode.

FIG. 6A is an image for explaining a mode in which the three modes of the independent type are carried out. FIG. 6B is an image for explaining a mode in which the three modes of the cooperation type are carried out.

The operation types of FIGS. 6A and 6B include the same features as those described with reference to FIGS. 5A and 5B. In the cooperation type of FIG. 6B, however, while the PW Doppler mode is successively carried out, the B mode and the color flow mode are carried out each time the PW Doppler mode is successively carried out several times. For this reason, a pulse repetition frequency in the PW Doppler mode has a longer period as compared with the case of FIG. 5B.

(Setting of Switching Frequency)

Next, a method for setting a switching frequency of power supply section 12 by control device 10 (switching-frequency setting section 10d) according to the present embodiment is described with reference to FIGS. 7 to 12. Control device 10 (switching-frequency setting section 10d) according to the present embodiment sets the switching frequency on the basis of a Doppler observation frequency band in the PW Doppler mode.

Figure 7:
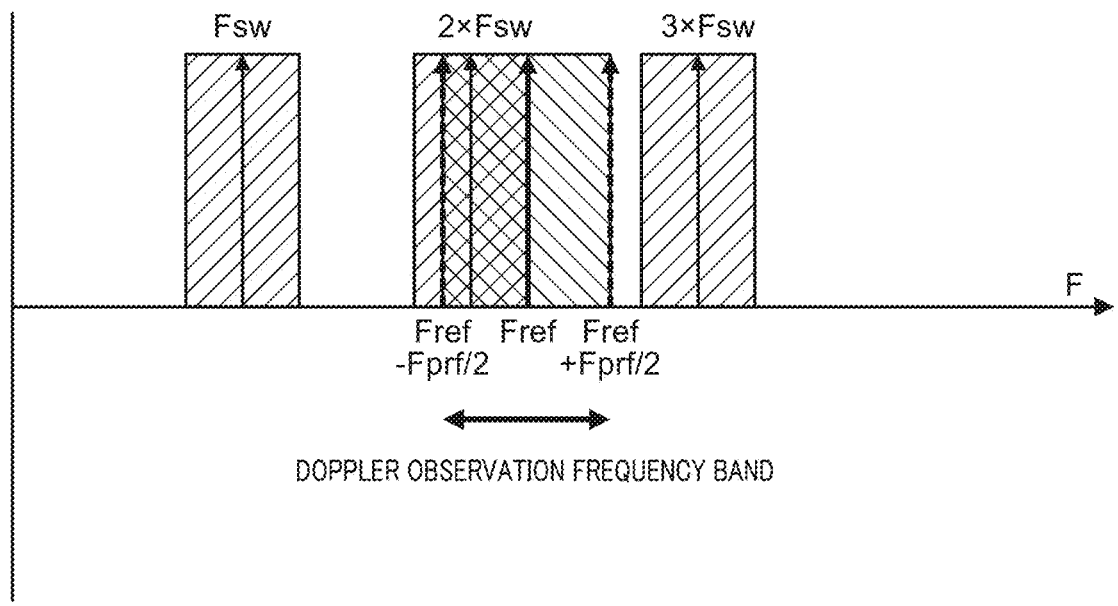
FIG. 7 is a graph for explaining the relation between a Doppler observation frequency band in a PW Doppler mode and a switching frequency.
Figure 8:
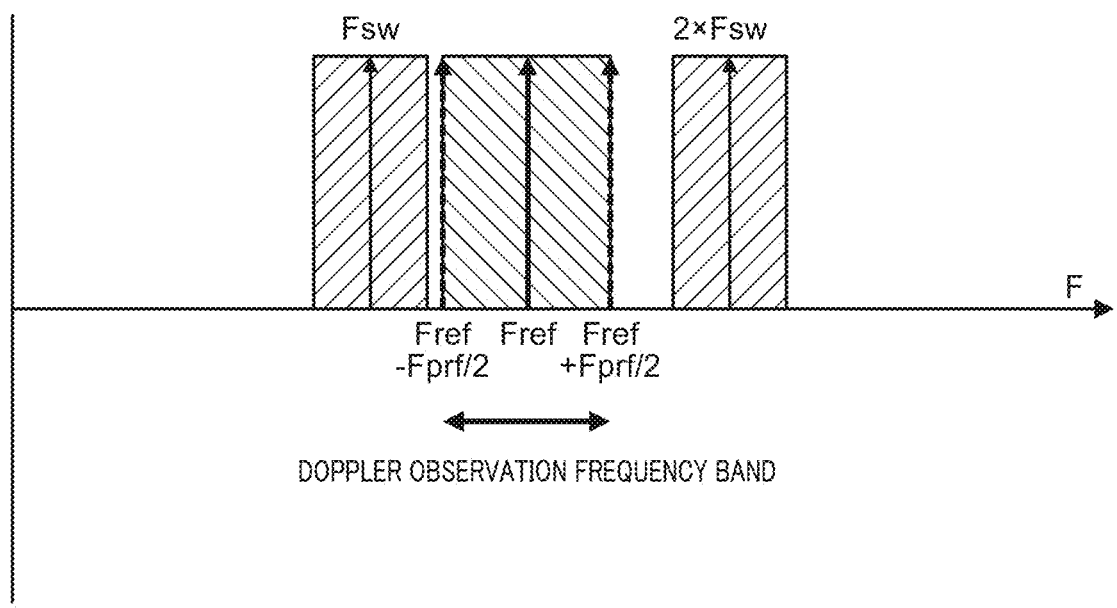
FIG. 8 is a graph for explaining the relation between the Doppler observation frequency band in the PW Doppler mode and the switching frequency.

FIGS. 7 and 8 are diagrams for explaining the relation between the Doppler observation frequency band in the PW Doppler mode and the switching frequency. The horizontal axes in the figures each indicate the frequency and the vertical axes each indicate the intensity of the reception signal or the switching noise at each frequency component. In the figures, "Fref" denotes the PW Doppler transmission frequency (reception reference frequency), "Fprf" denotes the PW Doppler pulse repetition frequency, and "Fsw" denotes the switching frequency of the DC/DC converter.

The Doppler shift frequency is a difference between frequency Fref of when an ultrasound pulse is transmitted and a frequency of when the ultrasound pulse is received, and is varied, depending on a blood flow velocity, within a frequency band ranging from Fref−ΔF to Fref+ΔF each of which is a frequency being smaller or greater by ΔF than transmission frequency Fref. At this time, the lower and upper limits Fref−ΔF and Fref+ΔF of the Doppler observation frequency band is limited by pulse repetition frequency Fprf according to the Nyquist sampling theorem, and accordingly the Doppler observation frequency band in which a Doppler shift frequency can be observed can be expressed by the following Expression 1:

$$Fref-(\tfrac{1}{2})Fprf \leq L \leq Fref+(\tfrac{1}{2})Fprf \quad \text{(Expression 1)}$$

wherein "L" denotes the Doppler observation frequency band, "Fref" denotes the transmission frequency (reference-wave frequency), and "Fprf" denotes the pulse repetition frequency.

In the meantime, a switching noise which occurs from power supply section 12 appears in a fundamental wave frequency and its harmonics of a switching signal. The fundamental wave (Fsw), second harmonic (Fsw×2), and third harmonic (Fsw×3) of the switching frequency are expressed as switching noise components in FIGS. 7 and 8. Note that the switching noise components are each illustrated in FIGS. 7 and 8 as a noise component having a width with respect to the switching frequency because the switching signal is a square wave, and/or the duty ratio of the DC/DC converter is changed successively depending on a power load, for example.

In a case where the switching noise component is superimposed on the Doppler observation frequency band as illustrated in FIG. 7, this switching noise component is mixed into the Doppler component, so that the switching noise appears on a frequency spectrum image.

In contrast, in a case where a switching noise component is not superimposed on the Doppler observation frequency band as illustrated in FIG. 8, the switching noise component is removed by the filtering processing and the like by PW Doppler processing section 5, so that the switching noise does not appear on a frequency spectrum image.

Figure 9:
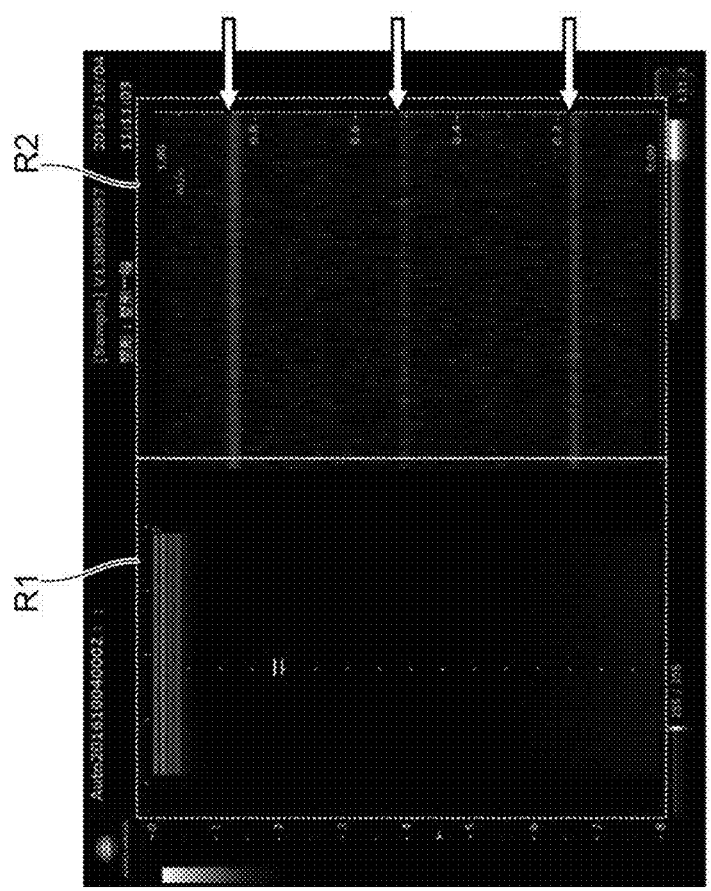
FIG. 9 illustrates an example of a displayed screen of a frequency spectrum image in which a switching noise is present.

FIG. 9 illustrates an example of a displayed screen of a frequency spectrum image including appeared switching noises. In FIG. 9, the switching noises are present in a continuous manner at some frequency positions (positions indicated by arrows) in the frequency spectrum image.

Accordingly, switching-frequency setting section 10d according to the present embodiment sets a switching frequency of the switching signal such that neither the fundamental wave frequency nor its harmonics (Fsw, 2×Fsw, 3×Fsw, . . . ) of the switching signal is included in the Doppler observation frequency band as in FIG. 8.

In this case, switching-frequency setting section 10d sets the switching frequency for each of the operation types in consideration that the Doppler observation frequency band is different depending on the operation type. In other words, constraints on the maximum pulse repetition frequency defining the Doppler observation frequency band are different for each operation type. For example, the B mode is carried out alternately with the PW Doppler mode in the cooperation type of the B mode and the PW Doppler mode (see FIG. 5B), so that the maximum pulse repetition frequency of the PW Doppler mode is constrained by the time of carrying out the B mode.

At this time, switching-frequency setting section 10d sets the switching frequency depending on a sample gate depth in consideration that the maximum pulse repetition frequency is different depending on the sample gate depth. In other words, the maximum pulse repetition frequency is limited by a round-trip time of an ultrasound pulse, that is, by a sample gate depth. For example, the maximum pulse repetition frequency is high (for example, 8 kHz) during detection at a shallow position, and is low (for example, 4 kHz) during detection at a deep position.

In this way, switching-frequency setting section 10d sets the switching frequency to satisfy the following Expressions 2 and 3, for example, in consideration of the maximum pulse repetition frequency to be determined depending on a sample gate depth and an operation type:

$$n*Fsw \leq Fref - (1/2)Fprfm \quad \text{(Expression 2)}$$

$$Fref + (1/2)Fprfm \leq (n+1)*Fsw \quad \text{(Expression 3)}$$

wherein "n" denotes a positive integer, "Fref" denotes the transmission frequency (reference-wave frequency), "Fsw" denotes the switching frequency, and "Fprfm" denotes the maximum pulse repetition frequency determined depending on a sample gate depth and an operation type.

In the above-mentioned Expressions 2 and 3, a pulse repetition frequency is set to the maximum value, so that the observable flow velocity range of the blood flow velocity is expanded to the maximum range. In this way, in the case of the operation of the independent type, for example, a switching frequency is set such that a flow velocity range is expanded (for example, the pulse repetition frequency is set to the maximum value), and a region where a frequency component of a switching noise is superimposed on a Doppler observation frequency band is reduced (switching noise is reduced). It is, however, sufficient to consider regulation conditions against a pulse repetition frequency that depends on the operation type to set the pulse repetition frequency, and the pulse repetition frequency does not have to be set to the maximum value.

It is more desirable, in this case, that, on the basis of the supposition that switching noises appear in frequency widths including higher and lower frequencies than the fundamental wave frequency or its harmonics of the switching signal as described above, switching-frequency setting section 10d sets the switching frequency such that such frequency widths are not further included in the Doppler observation frequency band. Switching-frequency setting section 10d sets the switching frequency to satisfy the following Expressions 4 and 5, for example, in consideration of the frequency widths (a frequency width that is substantially 1 to 10 times greater than pulse repetition frequency Fprfm is supposed here as a margin):

$$n*Fsw \leq Fref - (1/2)Fprfm*km \quad \text{(Expression 4)}$$

$$Fref + (1/2)Fprfm*km \leq (n+1)*Fsw \quad \text{(Expression 5)}$$

wherein "n" denotes a positive integer, "Fref" denotes the transmission frequency (reference-wave frequency), "Fsw" denotes the switching frequency, "Fprfm" denotes the maximum pulse repetition frequency determined depending on a sample gate depth and an operation type, and "km" denotes a margin coefficient (from 1 to 10 inclusive).

Figure 10:
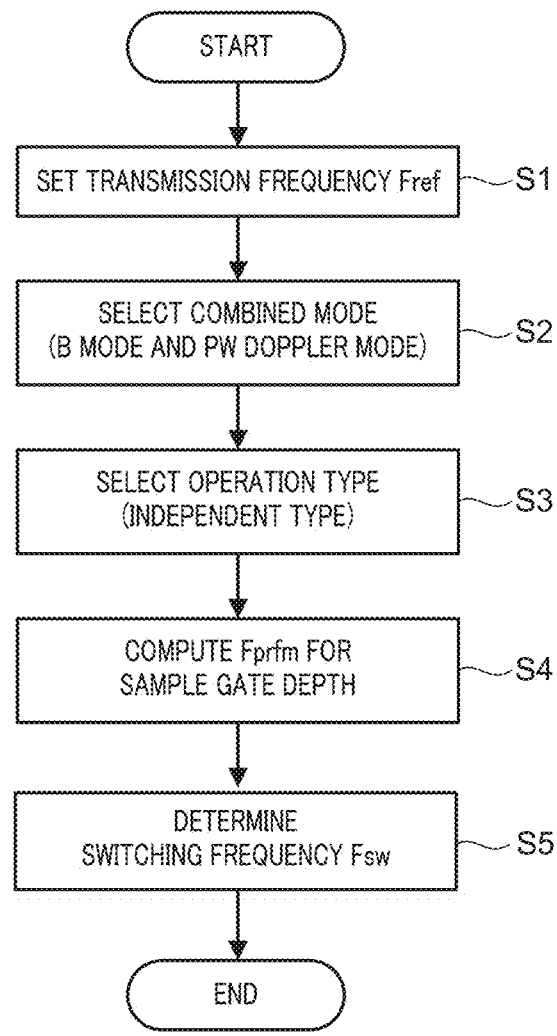
FIG. 10 is a flowchart which illustrates an example of operation of a control device for determination of a switching frequency.
Figure 11:
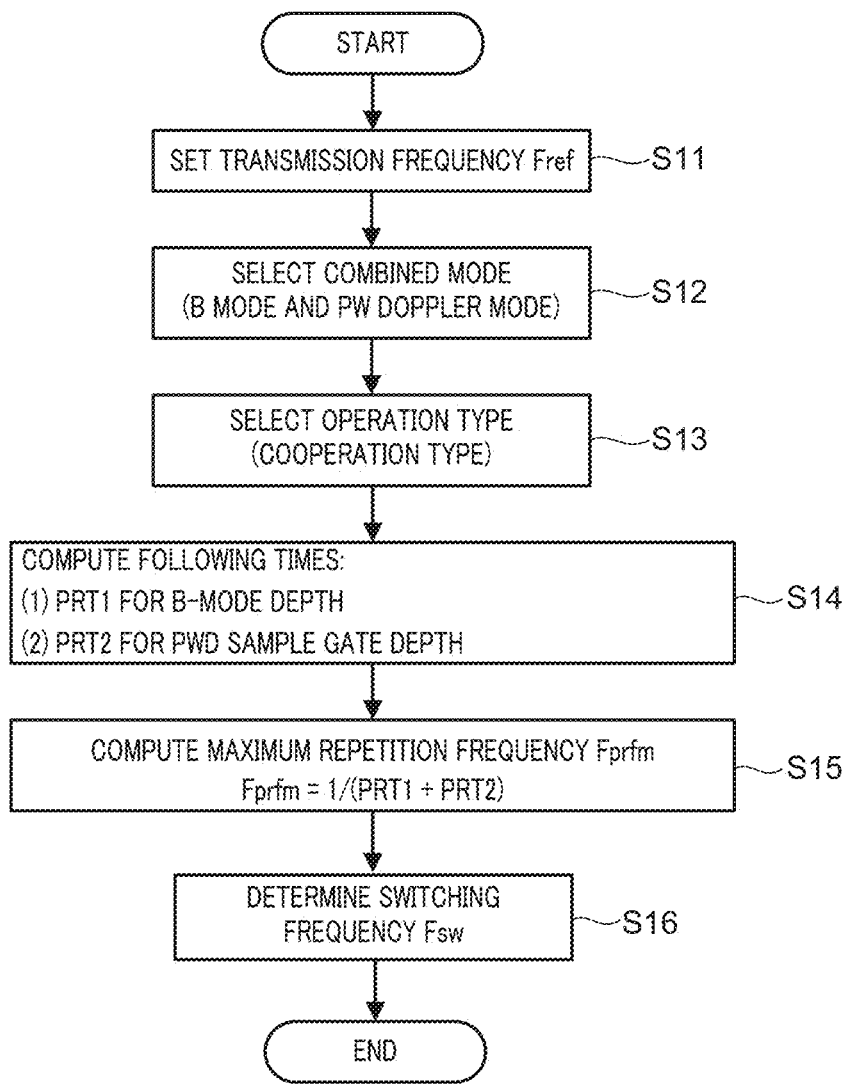
FIG. 11 is a flowchart which illustrates an example of operation of the control device for determination of a switching frequency.
Figure 12:
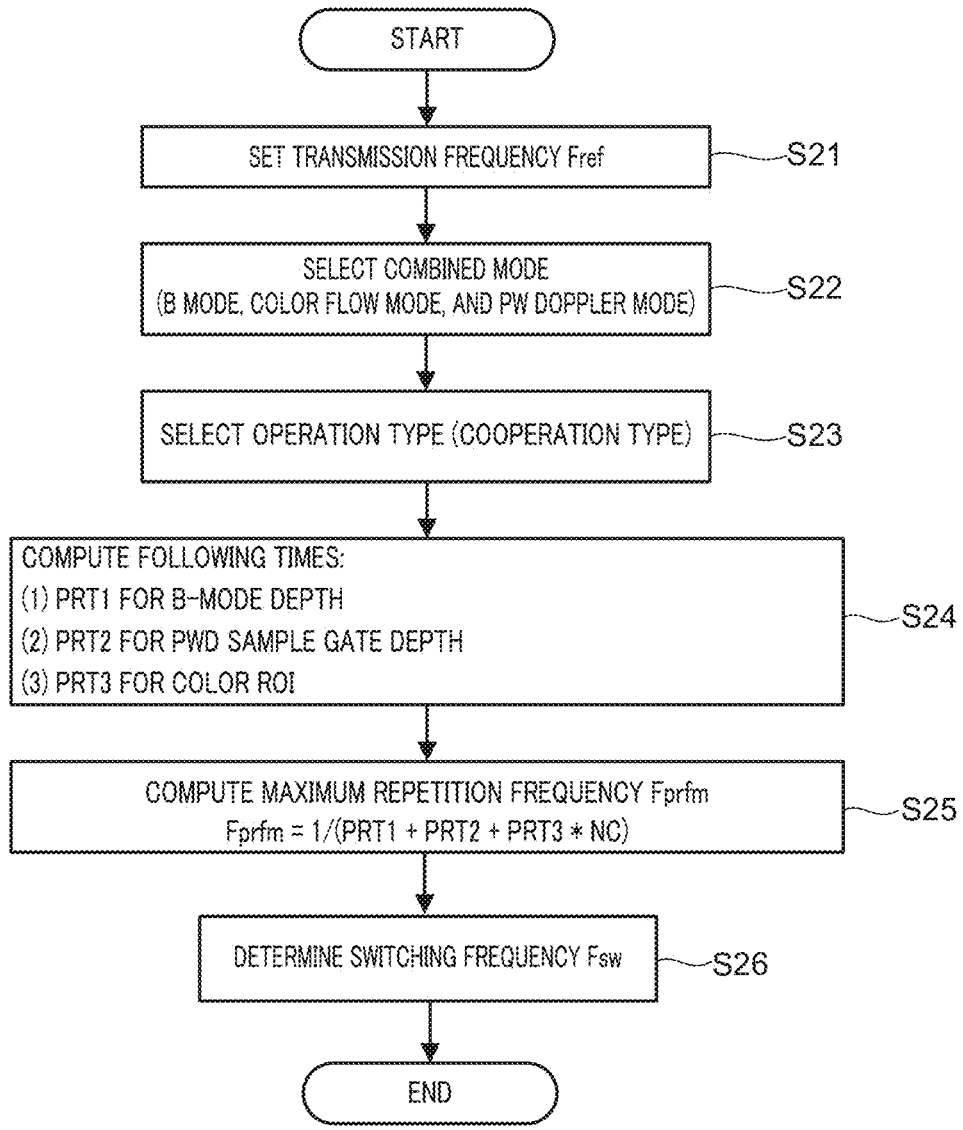
FIG. 12 is a flowchart which illustrates an example of operation of the control device for determination of a switching frequency.

FIGS. 10 to 12 are flowcharts which illustrate an example of operation of control device 10 during determination of switching frequency Fsw using the above-mentioned Expressions 2 and 3. Note that the processing in the flowcharts of FIGS. 10 to 12 is to be performed by control device 10 in accordance with a computer program, for example.

FIG. 10 illustrates an example of a process for determining switching frequency Fsw in the case where the operation in the PW Doppler mode of the independent type (corresponding to FIG. 5A) is performed in the combined operation mode of the B mode and the PW Doppler mode.

To begin with, control device 10 sets transmission frequency (reference wave frequency) Fref of an ultrasound pulse (step S1).

Next, control device 10 (operation-mode setting section 10b) sets an operation mode (step S2). By way of example, the combined operation mode of the B mode and the PW Doppler mode is set here by an operator's operation.

Next, control device 10 (operation-type setting section 10c) sets an operation type (step S3). By way of example, the independent type in the PW Doppler mode is set here by an operator's operation.

Next, control device 10 sets maximum pulse repetition frequency Fprfm corresponding to a sample gate depth (step S4).

Note in this case that control device 10 sets, as the maximum pulse repetition frequency, a maximum frequency which can be set in the system (analyzable limits and the like of FFT analysis section 12g), when maximum pulse repetition frequency Fprfm is greater than the maximum frequency which can be set in the system.

Control device 10 sets a Doppler observation frequency band with reference to transmission frequency (reference wave frequency) Fref of the ultrasound pulse and maximum pulse repetition frequency Fprfm set as described above, and sets switching frequency Fsw such that Expressions 2 and 3 are satisfied (step S5).

FIG. 11 illustrates an example of a process for determining switching frequency Fsw in the case where the B mode and the PW Doppler mode of the cooperation type are carried out in the combined operation mode (corresponding to FIG. 5B).

In the process of FIG. 11, similarly as in the process of FIG. 10, control device 10 sets transmission frequency (reference wave frequency) Fref of an ultrasound pulse (step S11), an operation mode (the combined operation mode of the B mode and the PW Doppler mode in this case) (step S12), an operation type (the cooperation type of the B mode and the PW Doppler mode in this case) (step S13), and maximum pulse repetition frequency Fprfm (steps S14 and S15).

In the case where the PW Doppler mode and the B mode of the cooperation type are carried out, however, the pulse repetition frequency is limited by the repetition time for carrying out the B mode. Accordingly, maximum pulse repetition frequency Fprfm in this case is computed based on repetition time PRT1 for carrying out the B mode that depends on a detection depth, and repetition time PRT2 for carrying out the PW Doppler mode that depends on a sample gate depth, maximum pulse repetition frequency Fprfm being computed, for example, using the following Expression 6:

$$Fprfm = 1/(PRT1 + PRT2) \quad \text{(Expression 6)}$$

wherein "Fprfm" denotes the maximum pulse repetition frequency, "PRT1" denotes the repetition time for carrying out the B mode that depends on a detection depth, and "PRT2" denotes the repetition time for carrying out the PW Doppler mode that depends on the sample gate depth.

Control device 10 refers to transmission frequency (reference wave frequency) Fref of the ultrasound pulse and maximum pulse repetition frequency Fprfm set as described above, so as to set switching frequency Fsw such that Expressions 2 and 3 are satisfied, in the same manner as described above (step S15).

FIG. 12 illustrates an example of a process for determining switching frequency Fsw in the case where the B mode, the PW Doppler mode, and the color flow mode of the cooperation type are carried out in the combined operation mode (corresponding to FIG. 6B).

In the process of FIG. 12, similarly as in the process of FIG. 10, control device 10 sets transmission frequency (reference wave frequency) Fref of an ultrasound pulse (step S21), an operation mode (the combined operation mode of the B mode, the PW Doppler mode, and the color flow mode in this case) (step S22), an operation type (the cooperation type of the B mode, the PW Doppler mode, and the color flow mode in this case) (step S23), and maximum pulse repetition frequency Fprfm (steps S24 and S25).

In the case where the PW Doppler mode operation, the B-mode operation, and the color flow mode operation are performed in the cooperation type, however, maximum pulse repetition frequency Fprfm is limited by the repetition time for performing the B-mode operation and the color flow mode operation. Accordingly, maximum pulse repetition frequency Fprfm in this case is computed, for example, using the following Expression 7, based on repetition time PRT1 for performing the B-mode operation that depends on a detection depth, and repetition time PRT2 for performing the PW Doppler mode operation that depends on a sample gate depth, and repetition time PRT3 for performing the color flow mode operation:

$$Fprfm = 1/(PRT1 + PRT2 + PRT3 * Nc) \quad \text{(Expression 7)}$$

wherein "Fprfm" denotes the maximum pulse repetition frequency, "PRT1" denotes the repetition time for performing the B-mode operation that depends on a detection depth, "PRT2" denotes the repetition time for performing the PW Doppler mode operation that depends on a sample gate depth, "PRT3" denotes the repetition time for performing the color Doppler mode operation that depends on a sample gate depth, and "Nc" denotes the number of times of the consecutive color-Doppler-mode operations.

Control device 10 refers to transmission frequency (reference wave frequency) Fref of the ultrasound pulse and maximum pulse repetition frequency Fprfm set as described above, so as to set switching frequency Fsw such that Expressions 2 and 3 are satisfied, in the same manner as described above (step S25).

As stated above, according to control device 10 of ultrasound diagnostic apparatus A according to the present embodiment, it is possible to set a switching frequency in consideration that the Doppler observation frequency band is different for each of the operation types in the combined operation mode. In this way, it is possible to set a switching frequency suitable for each operation type in the combined operation mode, and to reduce a switching noise superimposed on a detection result of a Doppler shift frequency. That is, the switching noise caused by a switching power supply can be prevented from being mixed into the detection result of the Doppler shift frequency.

To be specific, in the combined operation mode, there is a trade-off between the switching noise superimposition and the operation type. For example, when the operation of the independent type is performed, it is desired that the flow velocity range of the velocity pattern (Doppler observation frequency) is expanded even if superimposition of a switching noise is somewhat caused. In contrast, when the operation of the cooperation type is performed, it is desired to reduce the switching noise and the positional displacement in the pulsed Doppler mode. In this respect, according to control device 10 of ultrasound diagnostic apparatus A according to the present embodiment, a Doppler observation frequency band can be set depending of the operation type to satisfy these desires and a switching frequency can be set such that a switching noise to be superimposed on the Doppler observation frequency band can be reduced.

Other Embodiments

The present invention is not limited to the above-described embodiment, and various modified modes may be derived from the above-described embodiment.

Although a blood flow has been illustrated as an example of a target for detection of a Doppler shift frequency by ultrasound diagnostic apparatus A in the above-described embodiment, other moving tissues may be employed as the detection target.

In addition, a mode in which a switching frequency is set based on a Doppler observation frequency band in the PW Doppler mode has been illustrated as an example of the operation of control device 10 (switching-frequency setting section 10d) of ultrasound diagnostic apparatus A in the above-described embodiment.

In the case where the B mode and the color Doppler mode are carried out in the combined operation mode, however, a switching frequency may be set on the basis of a Doppler observation frequency band in the color Doppler mode.

In addition, although a control device in which functions of controlling section 10a, operation-mode setting section 10b, operation-type setting section 10c, and switching-frequency setting section 10d are implemented by a single computer has been illustrated as an example of control device 10 of ultrasound diagnostic apparatus A in the above-described embodiment, the functions may also be implemented by a plurality of computers. For example, controlling section 10a and switching-frequency setting section 10d may be implemented by separate computers.

In addition, although a control device in which processes of operation-mode setting section 10b, operation-type setting section 10c, and switching-frequency setting section 10d are serially performed has been illustrated as an example of control device 10 of ultrasound diagnostic apparatus A in the above-described embodiment, the processes may also be partly performed in parallel.

Although embodiments of the present invention have been described and illustrated in detail, it is clearly understood that the same is by way of illustration and example only and not limitation, the scope of the present invention should be interpreted by terms of the appended claims.

What is claimed is:

1. A control device of an ultrasound diagnostic apparatus, the ultrasound diagnostic apparatus having a switching power supply that produces an operational voltage, the ultrasound diagnostic apparatus being configured to transmit an ultrasound pulse repeatedly and to be capable of detecting a Doppler shift frequency from an ultrasound echo reflected from an inside of a subject, the control device comprising a hardware processor that:
- sets, from among a plurality of operation modes which include at least first and second operation modes in which pulse waveforms of ultrasound pulses to be transmitted are different from one operation mode to another, at least the first and second operation modes, for which observation results are to be simultaneously displayed on a screen;
- sets at least one operation type that defines transmission timing of ultrasound pulses in each of the first and the second operation modes; and
- sets a switching frequency of a switching signal used for driving the switching power supply, such that neither a fundamental frequency nor a harmonic of the switching signal is included in a Doppler observation frequency band to be determined based on the first and the second operation modes and on the operation type, wherein:
the plurality of operation modes include a pulsed Doppler mode,
the at least one operation type includes a second operation type in which, while ultrasound pulses related to the first operation mode are transmitted, an ultrasound pulse related to the second operation mode is transmitted between transmission of at least some of the ultrasound pulses related to the first operation mode,
in a case in which the hardware processor is configured to set the second operation type as the at least one operation type, set the pulsed Doppler mode as the first operation mode and set at least one operation mode other than the pulsed Doppler mode as the second operation mode, the hardware processor is configured to:
- determine a maximum pulse repetition frequency based on both of (i) a repetition time for carrying out the pulsed Doppler mode that depends on a sample gate depth and (ii) a repetition time for carrying out the at least one operation mode set as the second operation mode and that depends on a parameter that is set for performing ultrasound imaging in the second operation mode,
- determine the Doppler observation frequency band based on the determined maximum pulse repetition frequency, and
- set the switching frequency based on the determined Doppler observation frequency band such that neither the fundamental frequency nor a harmonic of the switching signal is included in the determined Doppler observation frequency band,
wherein the first and the second operation modes at least include a combination of the pulsed Doppler mode and a B mode, and
wherein the switching frequency is set to satisfy at least the following Expressions 1 and 2, based on a transmission frequency for transmission of the ultrasound pulses, and on a maximum pulse repetition frequency in the pulsed Doppler mode to be determined depending on the sample gate depth and the at least one operation type,
wherein the Expression 1 is:

$$n*Fsw \leq Fref-(½)Fprfm*km$$

wherein the Expression 2 is:

$$Fref+(½)Fprfm*km \leq (n+1)*Fsw$$

and
wherein n denotes a positive integer, Fref denotes the transmission frequency of ultrasound pulses, Fsw denotes the switching frequency, Fprfm denotes the maximum pulse repetition frequency to be determined depending on the sample gate depth and the at least one operation type, and km denotes a margin coefficient.

2. The control device according to claim 1, wherein:
the at least one operation type further includes a first operation type in which only ultrasound pulses related to the pulsed Doppler mode are successively transmitted.

3. The control device according to claim 1, wherein:
the switching power supply is a DC/DC converter of a switching drive system.

4. The control device according to claim 1, wherein:
the harmonic of the switching signal is any of a second to a fifth harmonics of the switching frequency.

5. An ultrasound diagnostic apparatus including the control device according to claim 1.

6. A control method for an ultrasound diagnostic apparatus, the ultrasound diagnostic apparatus having a switching power supply that produces an operational voltage, the ultrasound diagnostic apparatus being configured to transmit an ultrasound pulse repeatedly and to be capable of detecting a Doppler shift frequency from an ultrasound echo reflected from an inside of a subject, the control method comprising:
- setting, from among a plurality of operation modes which include at least first and second operation modes in which pulse waveforms of ultrasound pulses to be transmitted are different from one operation mode to another, at least the first and second operation modes, for which observation results are to be simultaneously displayed on a screen;
- setting at least one operation type that defines transmission timing of ultrasound pulses in each of the first and the second operation modes; and
- setting a switching frequency such that neither a fundamental frequency nor a harmonic of a switching signal used for driving the switching power supply is included in a Doppler observation frequency band to be determined based on the first and the second operation modes and on the operation types, wherein:
the plurality of operation modes include a pulsed Doppler mode,
the at least one operation type includes a second operation type in which, while ultrasound pulses related to the first operation mode are transmitted, an ultrasound pulse related to the second operation mode is transmitted between transmission of at least some of the ultrasound pulses related to the first operation mode,
the second operation type is set as the at least one operation type, the pulsed Doppler mode is set as the first operation mode and at least one operation mode other than the pulsed Doppler mode is set as the second operation mode, and the method further comprises:
- determining a maximum pulse repetition frequency based on both of (i) a repetition time for carrying out the pulsed Doppler mode that depends on a sample gate depth and (ii) a repetition time for carrying out the at least one operation mode set as the second operation mode and that depends on a parameter that is set for performing ultrasound imaging in the second operation mode, determining the Doppler observation frequency band based on the determined maximum pulse repetition frequency, and setting the switching frequency based on the determined Doppler observation frequency band such that neither the fundamental frequency nor a harmonic of the switching signal is included in the determined Doppler observation frequency band, the first and the second operation modes at least include a combination of the pulsed Doppler mode and a B mode, and wherein the switching frequency is set to satisfy at least the following Expressions 1 and 2, based on a transmission frequency for transmission of the ultrasound pulses, and on a maximum pulse repetition frequency in the pulsed Doppler mode to be determined depending on the sample gate depth and the at least one operation type:

wherein the Expression 1 is:

$n*Fsw \leq Fref-(1/2)Fprfm*km$ wherein the Expression 2 is:

$Fref+(1/2)Fprfm*km \leq (n+1)*Fsw$ and wherein n denotes a positive integer, Fref denotes the transmission frequency of ultrasound pulses, Fsw denotes the switching frequency, Fprfm denotes the maximum pulse repetition frequency to be determined depending on the sample gate depth and the at least one operation type, and km denotes a margin coefficient.

* * * * *